United States Patent [19]

Donnery

[11] Patent Number: 4,771,548
[45] Date of Patent: Sep. 20, 1988

[54] BIPLANE GONIOMETER

[76] Inventor: Joseph P. Donnery, 3407 Grand, Apt. 311, Des Moines, Iowa 50312

[21] Appl. No.: 67,204

[22] Filed: Jun. 29, 1987

[51] Int. Cl.$^4$ .............................................. G01B 9/10
[52] U.S. Cl. ...................................... 33/512; 33/1 N; 33/534; 33/415; 33/471
[58] Field of Search ................. 33/471, 512, 515, 511, 33/424, 426, 415, 534, 195, 468, 465, 403, 1 N

[56] References Cited

U.S. PATENT DOCUMENTS

| | | | |
|---|---|---|---|
| 832,060 | 10/1906 | Holmquist | 33/195 |
| 1,550,755 | 8/1925 | Steinle . | |
| 1,590,499 | 6/1926 | Cozad | 33/512 |
| 1,947,448 | 2/1934 | Ahola | 33/465 |
| 2,111,871 | 3/1938 | Nissenbaum . | |
| 3,229,372 | 1/1966 | Quashnock et al. . | |
| 3,270,420 | 9/1966 | Simril . | |
| 3,273,246 | 9/1966 | Siberini | 33/470 |
| 4,531,296 | 7/1985 | Veeze | 33/468 |
| 4,611,407 | 9/1986 | vanGorp . | |
| 4,660,293 | 4/1987 | Kovacs | 33/471 |

FOREIGN PATENT DOCUMENTS 51358  3/1936  Denmark ............................. 33/471

OTHER PUBLICATIONS

"Ankle Function: Measurement and Functional Bracing of the Fractured Ankle", by David Segal, M. D., *The Foot and Ankle,* 1980.

"Measurement of Joint Motion: A Guide to Goniometry, Cyntia Clair Norkin and D. Joyce White, 1985.

"The Biplane Goniometer: A New Device for Measurement of Ankle Dorsiflexion", Joseph P. Donnery, May 1987.

Preston Equipment for Rehabilitation and Special Education 1986–1987 Catalog, p. 4.

*Primary Examiner*—William D. Martin, Jr.
*Attorney, Agent, or Firm*—Henderson & Sturm

[57] ABSTRACT

A biplane goniometer including a platform having a first planar surface thereon. An indicia mark on the side of the platform is disposed in plane parallel to the first planar surface. A flexible, stable arm is pivotally attached to the platform and the stable arm is disposed in a plane substantially perpendicular to the first planar surface. The stable arm has a reference line disposed longitudinally thereon. Measuring data, including calibrated numbers, is disposed on the stable arm in an arc about the axis for measuring the arc between the indicia mark on the platform and the reference line on the stable arm.

4 Claims, 2 Drawing Sheets

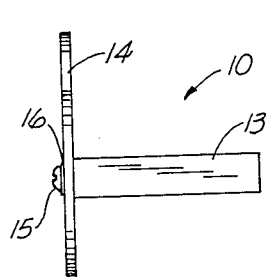
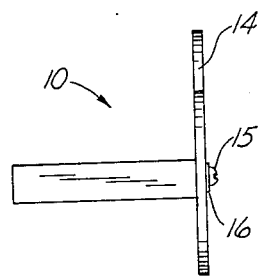
Fig. 4   Fig. 5
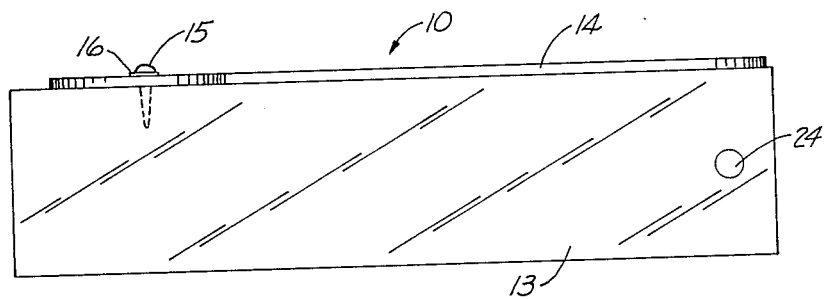
Fig. 6
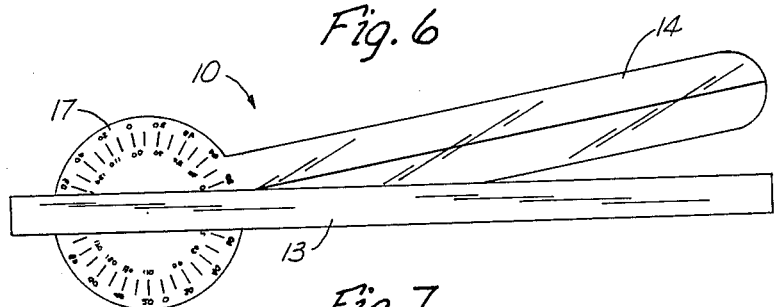
Fig. 7
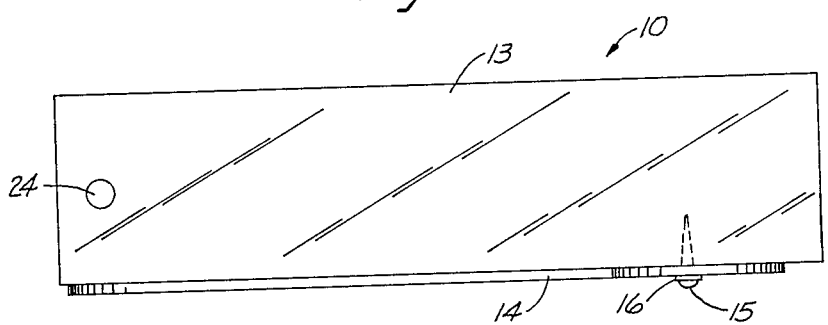
Fig. 8

BIPLANE GONIOMETER

TECHNICAL FIELD

The present invention relates generally to a goniometer for measuring joint angles and more particularly to a novel biplane goniometer which is particularly adapted to measure the dorsiflexion movement of the foot at the ankle upwardly toward the knee along the sagittal plane.

BACKGROUND ART

Medical practitioners must from time to time measure the dorsiflexion of the human foot for medical purposes. Dorsiflexion is defined as the movement of the foot at the ankle upwardly toward the knee along the sagittal plane. In order to measure dorsiflexion, a more or less standard goniometer is used and may be similar to the goniometer shown in U.S. Pat. No. 3,270,420 which has substantially two flat members pivoted together and having a scale thereon for measuring the amount of pivoting of one with respect to the other.

To measure dorsiflexion with such a device, a reference line on one of the goniometer arms is aligned with the lateral midline of the lower leg using the head of the fibula as a reference point. The other arm of the goniometer is placed at 90° with respect to the first arm and the axis of pivoting between the two arms is more or less aligned with the pivotal axis of the foot with respect to the leg. Then the foot is pivoted manually as much as is possible, and this angle of movement between the starting and finishing positions is measured and is considered to be the dorsiflexion. Normally, this assessment is done while the patient is sitting with the patient's feet off the ground.

A problem with conventional goniometer instrumentation for measuring dorsiflexion is that it does not allow the medical examiner to consider the manner in which the entire foot interacts with the ground while performing ankle dorsiflexion assessment.

Another problem associated with currently available instrumentation for the assessment of ankle dorsiflexion is that medical examiners use a variety of anatomical landmarks to determine how the two arms of the goniometer are aligned with the leg, foot and ankle. This results in a lack of consistency among professionals claiming to measure the same motion. The actual measurement as obtained with currently available instrumentation therefore becomes subjective because there is no common line used to represent the transverse plane. Furthermore, dorsiflexion assessment is awkward and cumbersome with the currently available instrumentation. Manipulation of the subtalar joint, which is important in proper dorsiflexion assessment, can distort the dorsiflexion measurement using currently available instrumentation.

Consequently, there is a need for a goniometer structure which will overcome the aforementioned problems and facilitate consistent, objective dorsiflexion assessment.

DISCLOSURE OF THE INVENTION

The present invention relates to a biplane goniometer including a platform having a first planar surface thereon. An indicia mark on the side of the platform is disposed in a plane parallel to the first planar surface. A flexible, stable arm is pivotally attached to the platform and the stable arm is disposed in a plane substantially perpendicular to the first planar surface. The stable arm has a reference line disposed longitudinally thereon. Measuring data, including calibrated numbers, is disposed on the stable arm in an arc about the axis for measuring the arc between the indicia mark on the platform and the reference line on the stable arm.

The method of using the goniometer referred to above includes the steps of placing a first planar surface of the platform on the bottom of a voluntarily dorsiflexed human foot, aligning the reference line of the stable arm along the line extending between the center of the fibular head and the lateral malleolus. The foot is then dorsiflexed by the examiner through any residual dorsiflexion range of motion and the angle of movement is measured by reading the data measuring information on the stable arm.

An object of the present invention is to provide an improved goniometer.

Another object of the present invention is to provide a goniometer for facilitating objective and consistent assessment of ankle dorsiflexion by elimination of the variety of anatomical landmarks currently used.

An additional object of the present invention is to provide a goniometer which allows the entire plantar surface of the foot to rest on a uniform surface during ankle dorsiflexion assessment which more truly represents its functional interaction with the ground.

A further object of the present invention is to provide a goniometer of the aforementioned type which is economical to produce and simple to use.

Other objects, advantages, and novel features of the present invention will become apparent from the following detailed description of the invention when considered in conjunction with the accompanying drawings.

BRIEF DESCRIPTION OF THE DRAWINGS

FIG. 4 is a view of one end of the biplane goniometer shown in FIG. 3;

FIG. 5 is a view from the opposite end from that shown in FIG. 4;

FIG. 6 is a top view of the goniometer of FIG. 3;

FIG. 7 is a view from the opposite side from that shown in FIG. 3; and

FIG. 8 is a bottom view of the goniometer shown in the other views.

BEST MODE FOR CARRYING OUT THE INVENTION

Figure 1:
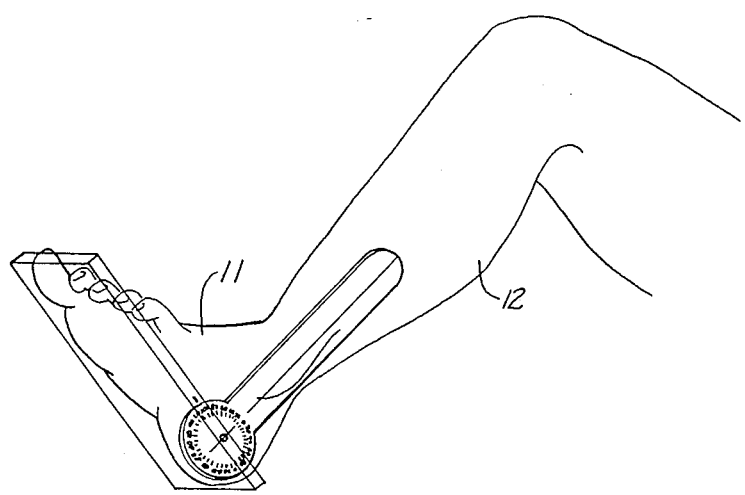
FIG. 1 is a perspective view of a preferred embodiment of the present invention shown in position with the ankle in neutral.

Referring now to the drawings wherein like reference numerals designate identical or corresponding parts throughout the several views, FIG. 1 shows a perspective view of a goniometer (10) constructed in accordance with the present invention and shown in conjunction with a human foot (11) and human leg (12). Referring to FIGS. 3 through 8, it is noted that a plexiglass platform (13) has a clear, plastic, flexible stable arm (14) pivotally attached thereto by a screw (15) and washer (16). Platform (13) has an opening (24) therein so it can be stored on a nail or hook in a wall. The screw (15) extends through an opening in the center of the circular portion (17) of the stable arm (14). The stable arm (14) has a reference line (18) thereon and one side of the platform (13) has an indicia mark (19) thereon.

The circular portion of the stable arm (18) has an outer scale which goes from 0° to 90° and then back to 0 on each side thereof. The inner scale goes from 0° to 180° on the opposite thereof and back to 0. It is not so important as to what the scale is on these numbers, but some numbers must be present in order to measure the degree of dorsiflexion.

Figure 2:
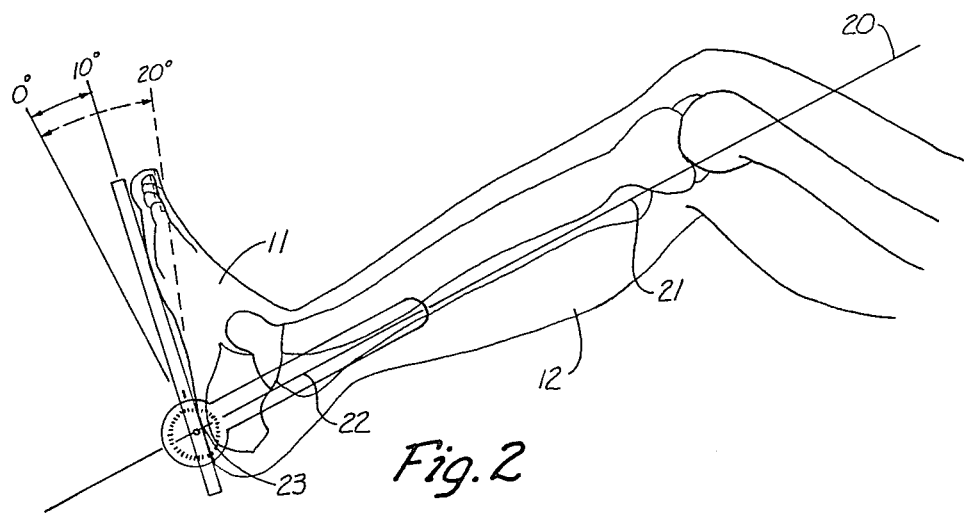
FIG. 2 is a side elevational view of the preferred embodiment shown in FIG. 1 and showing the actual measurement of ankle dorsiflexion.
Figure 3:
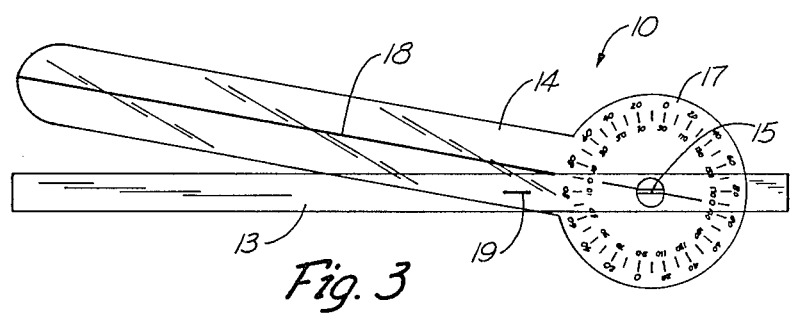
FIG. 3 is an enlarged side elevational view of the preferred embodiment of the present invention in one position thereof.

In order to utilize the biplane goniometer (10) as shown in the drawings, the patient would be in the supine or the sitting position and the patient is asked to dorsiflex the foot as much as possible. The medical examiner would then position the biplane goniometer (10) to the position shown in FIG. 2 wherein the platform (13) is placed against the bottom of the foot (11) and the reference line (18) is generally aligned with a line (20) which extends through the center of the fibular head (21) and the center (22) of the lateral malleolus with the reference line (18) being in alignment with the line (20) as shown in FIG. 2 and with the plantar surface of the foot resting on the platform (13). The gauge would then be visible to the medical examiner at the plantar lateral heel (23).

It is important to note that the stable arm (18) would be on the outside of the foot (11) and not on the inside during this measurement. The medical examiner would then grasp the platform (13) and the foot (11) about the first metatarsophalangeal region and then manipulate the subtalar joint to neutral or to a slight inversion while the patient relaxes. The appropriate force is then applied to the plantar surface of the platform, bringing the ankle to the dorsiflexion range extreme. Once the ankle has been so flexed as much as possible, measurement is ascertained by reading the numbers on the scale closest to the indicia mark (19) on the platform (13). For example, looking at FIG. 3, it is noted that the reference line (18) is 10° away from the line (19). It is also noted that the stable arm (18) is transparent so that the indicia line (19) can be viewed therethrough.

Looking again to FIG. 2, it is noted that the degree of dorsiflexion shown in solid lines is 10° and the dashed lines indicating 20° could be measured if the foot were to be flexed twice as much as is shown in solid lines.

Accordingly, it will be appreciated that the preferred embodiment shown herein does indeed accomplish the aforementioned objects. Obviously, many modifications and variations of the present invention are possible in light of the above teachings. It is therefore to be understood that, within the scope of the appended claims, the invention may be practiced otherwise than as specifically described.

I claim:

1. A biplane goniometer for measuring the joint angles during the dorsiflexion movement of a human foot at the ankle upwardly toward the knee along the sagittal plane; wherein, the biplane goniometer comprises:
   a movable rigid platform having a first generally elongated rectangular planar surface dimensioned to receive and support the bottom of a human foot;
   an indicia mark on the side of said platform, said mark being disposed in a second plane parallel to said first planar surface;
   an elongated stable arm, said stable arm lying substantially in a plane perpendicular to said first planar surface, and having a reference line disposed longitudinally on said stable arm;
   means for pivotally attaching said stable arm to said movable platform about an axis passing substantially through said second planar surface at a location proximate to, but spaced from one end of said platform; wherein, the sagittal plane between the ankle and the knee may be positioned above the means for pivotally attaching said stable arm to said movable platform while the bottom of the foot rests upon the first planar surface; and
   measuring data means including calibrated numbers disposed on said stable arm generally in an arc about said axis for measuring the arc between said indicia mark on said movable platform and the reference line on said stable arm.

2. The goniometer of claim 1 wherein said stable arm is constructed of flexible material.

3. The goniometer of claim 2 wherein said stable arm is constructed of transparent material.

4. A method of using a goniometer to measure the angle of flexion of a human foot wherein the goniometer includes: an elongated generally rectangular rigid platform having a top surface that is dimensioned to support a human foot, and a relatively movable elongated stable arm pivotally disposed along one side of said rigid platform, wherein the stable arm is provided with an elongated reference line, including the steps of:
   (a) placing the first planar surface of the platform on the bottom of a human foot;
   (b) aligning the reference line along a line extending between the center of the fibular head and the lateral malleolus while keeping the stable arm in contact with the outside of the foot and leg;
   (c) pivoting said foot with said platform as much as desired; and
   (d) measuring the angular displacement between said reference line and said top surface to determine the angle of flexion of said foot between a normal standing position and the position of the foot after the foot has been flexed.

* * * * *